United States Patent [19]

Atkinson

[11] Patent Number: 5,219,352
[45] Date of Patent: Jun. 15, 1993

[54] SKIN GRAFT PREPARATION APPARATUS

[75] Inventor: Robert W. Atkinson, Dover, Ohio

[73] Assignee: Zimmer, Inc., Warsaw, Ind.

[21] Appl. No.: 785,089

[22] Filed: Oct. 30, 1991

Related U.S. Application Data

[60] Division of Ser. No. 656,471, Feb. 19, 1991, abandoned, which is a continuation of Ser. No. 374,833, Jul. 3, 1989, Pat. No. 5,004,468.

[51] Int. Cl.⁵ .......................................... A61B 17/322
[52] U.S. Cl. ..................................... 606/132; 83/678; 83/658
[58] Field of Search .................. 606/132; 83/678, 658

[56] References Cited

U.S. PATENT DOCUMENTS

| | | | |
|---|---|---|---|
| 3,076,462 | 2/1963 | Meek et al. | 606/132 |
| 3,358,688 | 12/1967 | Tanner | 606/132 |
| 3,472,228 | 10/1969 | Tanner | 606/132 |
| 3,640,279 | 2/1972 | Brown et al. | 606/132 |

FOREIGN PATENT DOCUMENTS 2473302  7/1981  France ............................. 606/132

*Primary Examiner*—Michael H. Thaler
*Attorney, Agent, or Firm*—H. Jay Spiegel

[57] ABSTRACT

A skin graft preparation apparatus is disclosed which includes the use of an extruded skin carrier having guide surfaces thereon which mesh with corresponding guide surfaces on one of the rollers of the apparatus. The device includes structure allowing easy removal, replacement and exchange of the cutter mechanism thereof so that cutters of different ratios may easily be interchanged. Springs engaging respective ends of the cutter mechanism allow slight upward movements thereof to accommodate to skin of varying thickness.

15 Claims, 5 Drawing Sheets

SKIN GRAFT PREPARATION APPARATUS

This application is a division of application Ser. No. 07/656,471, filed Feb. 19, 1991, now abandoned, which is a continuation of application Ser. No. 07/374,833, filed Jul. 3, 1989, now U.S. Pat. No. 5,004,468.

BACKGROUND OF THE INVENTION

The present invention relates to a skin graft preparation apparatus. Such apparatuses are generally known in the prior art. The purpose for such devices is to prepare skin for a skin graft in such a way that a small area of skin may be expanded to be grafted over a larger area on the patient. In this regard, an article by R. Peeters and A. Hubens, published in *Burns*, 1988, Vol. 14, No. 3, pp. 238-240, and titled "The Mesh Skin Graft—True Expansion Rate", discusses the effectiveness of pretreatments of skin used for skin grafts. In the article, it was concluded that the expansion of skin after treatment in prior art skin graft preparation apparatuses never achieved the results which were claimed. Thus, for example, where a cutter mechanism was provided which was claimed to achieve a 3:1 expansion ratio, not a single treated skin graft reached this ratio. In fact, a significant number failed to even reach a 1.5:1 expansion ratio.

A further discussion of prior art skin graft preparation apparatuses is found in a publication titled "Treating the Burn Wound", pp. 97 through 107 thereof in particular. FIG. 6-5 thereof and the accompanying text describes and explains the uses of the Tanner Mesher, which is specifically described in U.S. Pat. No. 3,472,228 to Tanner, Jr. In this device, the cutting mechanism thereof is designed to provide a single ratio, for example, one of 1.5:1, 3:1, 6:1 or 9:1. It is important to note that each Tanner mesher machine incorporates a single one of the above-listed ratios therein and cutters of different ratios may not be interchanged therewith.

The following prior art is also known to applicant:

U.S. Pat. No. 3,472,228 to Tanner, Jr. was described above; additionally, U.S. Pat. No. 3,593,985 appears to disclose a refinement of the carrier mechanism of the Tanner, Jr. device described in U.S. Pat. No. 3,472,228.

U.S. Pat. No. 3,358,688 to Tanner, Jr. discloses a method of preparing skin for use in a skin graft. In this patent, two means are identified of meshing skin. A first method depicts a moving transverse bed of alternating cutters which travel beneath a pressure roll. A carrier made up of a stripping sheet and a pressure sheet between which a piece of skin is contained passes between the bed of cutters and the pressure roll. When the carrier and skin pass beneath the pressure roll, a cutting action is carried out. The second means uses the same general concept; however, the cutting bed has been transformed into a circular bed or cutting roll between which the carrier and skin pass. The alternating cuts are caused by machined areas within the length of the knife edge which are either circular or straight. The machined areas between the adjacent knife edges alternate.

U.S. Pat. No. 3,640,279 to Brown, et al. discloses a cylindrical bottom roll which utilizes angular slots as a means of providing an action similar to that of a flat grooved derma-carrier. There is nothing in this patent to teach or suggest changing of the angle of the slots to alter the length of a cut, nor as to a means to interchange a variety of bottom rolls having differently angled grooves.

U.S. Pat. No. 4,773,418 to Hettich discloses a device designed to be used to manufacture a skin graft by seeding skin from a cadaver with skin of a patient. The teachings of this patent are believed to be only generally related to the teachings of the present invention.

As such, a need has developed for a skin graft preparation apparatus which will achieve claimed ratios between the original area of the grafting skin and the area which is covered by the skin during a grafting procedure. A further need has developed for a skin graft preparation apparatus which includes parts which may easily be exchanged so as to avoid the significant expense of purchase of a single skin graft preparation apparatus for each desired ratio.

A further need has developed for a skin graft preparation apparatus having a superior means for guiding skin through the cutter mechanism thereof to achieve optimal results.

It is with these needs in mind that the present invention was developed.

SUMMARY OF THE INVENTION

The present invention relates to a skin graft preparation apparatus. The present invention includes the following interrelated aspects and features:

(a) In a first aspect, the inventive apparatus includes a housing including a base on which support means consisting of two upstanding spaced supports are provided.

(b) The above-described upstanding supports support therebetween roller means consisting of two vertically spaced rollers. The bottom roller which is closest to the base comprises a guide roller including alternating regions of respective greater and lesser diameter. The top roller, which is slightly spaced from the bottom roller, comprises a cutter roller having grooves formed therein with sharp edges.

(c) With further reference to the top roller, the grooves are formed preferably in a turning operation wherein a plurality of closely spaced cutter heads are simultaneously engaged on the surface of the roller and are moved laterally together as the roller rotates on a turning machine so that a plurality, corresponding to the number of cutter heads, of spiral-shaped grooves, parallel to one another, are formed on the surface of the roller. The number of these grooves which are formed on the cutter roller determines the ratio of expansion of the grafted skin.

(d) A carrier device is provided to carry skin which is to be treated by the inventive apparatus through the cutter roller. This carrier device consists of an elongated member having a bottom surface with regions of alternating thickness corresponding to the alternating regions of thickness on the guide roller, as well as a flat top surface on which skin to be treated by the skin graft preparation apparatus is placed. The bottom surface of the carrier device enmeshes with the alternating regions of the guide roller to guide the carrier device through the apparatus in a predetermined manner. Skin placed on the top surface of the carrier device is carried through the cutter roller to cause a particular pattern of cuts to be formed thereon, which pattern best facilitates expansion of the skin during a grafting procedure.

(e) A cover means consisting of a cover is pivotably mounted on the upstanding supports in such a manner that the cover may be loosened and pivoted to allow removal of the cutter roller and exchange of the cutter roller with a cutter roller of different ratio. Each cutter roller has bearings thereon facilitating easy rotation thereof. These bearings are mounted within the walls of the upstanding supports in such a manner that when the cover is pivoted to its closed position, resilient biasing means are interposed between respective sides of the cover and respective bearings of the cutter roller. In this way, the cutter roller can slightly move up and down to accommodate to skin having slight variations in thickness, to avoid binding of the skin in the apparatus and to best facilitate the smooth operation therof.

As such, it is a first object of the present invention to provide an improved skin graft preparation apparatus.

It is a further object of the present invention to provide such an apparatus having structure allowing exchange of the cutter roller thereof with cutter rollers of differing ratios of meshing of skin.

It is a further object of the present invention to provide such an apparatus having mounting means for the cutter roller thereof which allows slight up and down movements of the cutter roller to accommodate to variations in skin thickness.

It is a yet further object of the present invention to provide such an apparatus with a carrier device designed to accurately guide skin through the cutter roller thereof.

These and other objects, aspects and features of the present invention will be better understood from the following detailed description of the preferred embodiment when read in conjunction with the appended drawing figures.

SPECIFIC DESCRIPTION OF THE PREFERRED EMBODIMENTS

Figure 1:
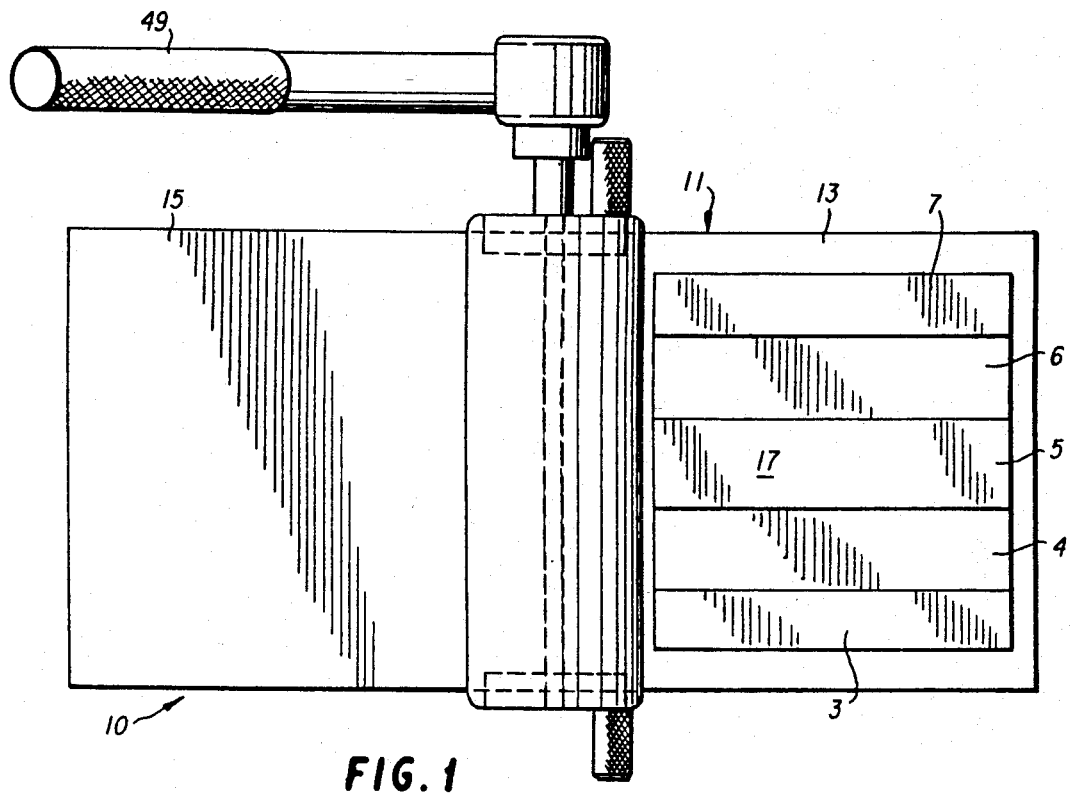
FIG. 1 shows a top view of the present invention.

With reference, first, to FIGS. 1-5, it is seen that the inventive apparatus is generally designated by the reference numeral 10 and is seen to include a housing 11 forming a base having a first end 13 and a second end 15. On the end 13 of the housing 11, a platform 17 is provided for a purpose to be described in greater detail hereinafter.

Centrally located on the base 11 on two opposed supports 19 and 21, with the support 19 being bolted to the base 11 by bolts 23 and 25, and with the support 21 being bolted to the base 11 by bolts 27 and 29.

Figure 2:
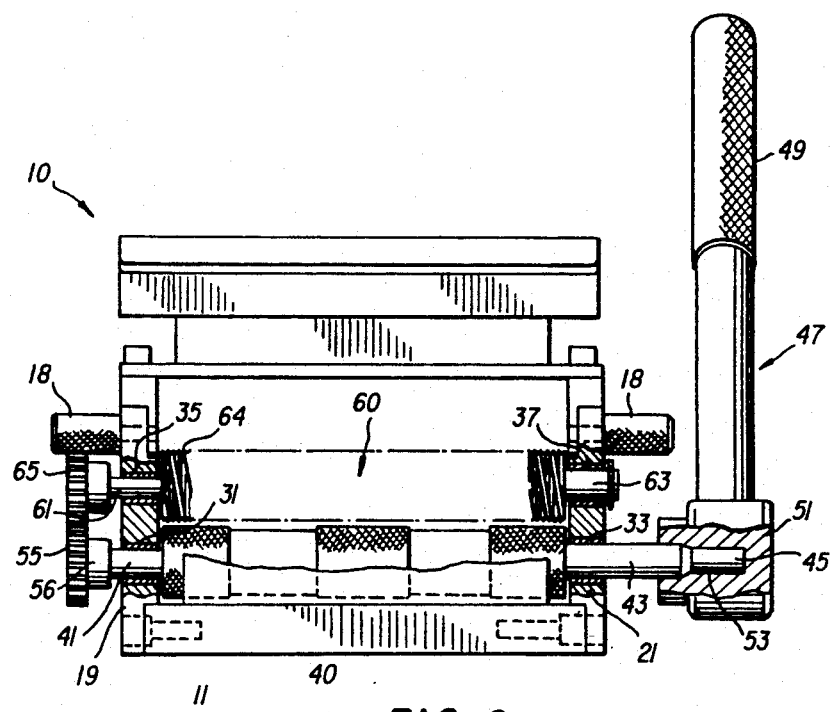
FIG. 2 shows a front view of the present invention.

As best seen in FIG. 2, the supports 19, 21 include a first pair of aligned openings 31, 33 and a second pair of aligned openings 35 and 37. The openings 31, 33 are provided to rotatably receive the guide roller 40 while the openings 35 and 37 are provided to rotatably receive the cutter roller 60.

As seen in FIG. 2, the guide roller 40 includes axles 41, 43 which respectively extend through the openings 31, 33, and the cutter roller 60 has axles 61, 63 which respectively extend through the openings 35, 37 in the supports 19, 21.

The axle 43 of the guide roller 40 extends out to a coupling portion 45 designed to transmit forces from actuator means including an actuator handle 47 including a handle portion 49 and a chuck portion 51 having a recess 53 therein designed to couple with the coupling portion 45 of the axle 43.

Drive means interconnects the rollers together. In this regard, the axle 41 of the guide roller 40 has mounted thereon a gear 55 which is enmeshed with a gear 65 mounted on axle 61 of the cutter roller 60. Thus, rotations of the handle 47 will cause corresponding rotations of the guide roller 40 and, via the axle 41, gear 55, gear 65 and axle 61, corresponding rotations of the cutter roller 60 but in an opposite direction thereof. Thus, clockwise rotations of the handle 47 will result in clockwise rotations of the guide roller 40 and counterclockwise rotations of the cutter roller 60.

Figure 4:
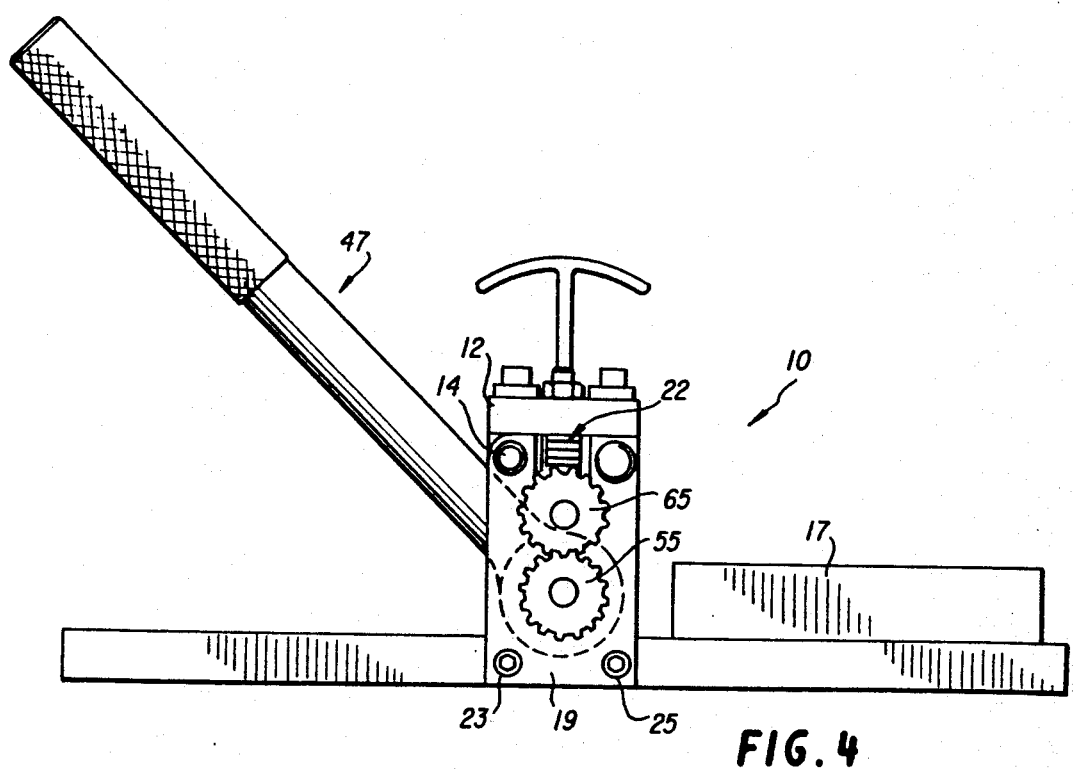
FIG. 4 shows a left side view of the present invention.
Figure 5:
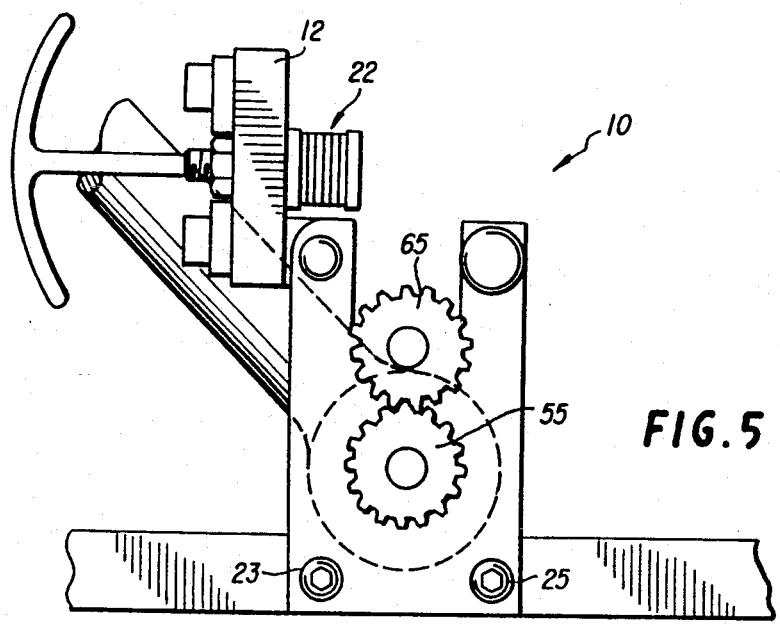
FIG. 5 shows a left side view, but with the cover of the device pivoted to allow changing of the cutter roller thereof.

FIGS. 4 and 5 best illustrate the enmeshing of the gears 55, 65.

Figure 6:
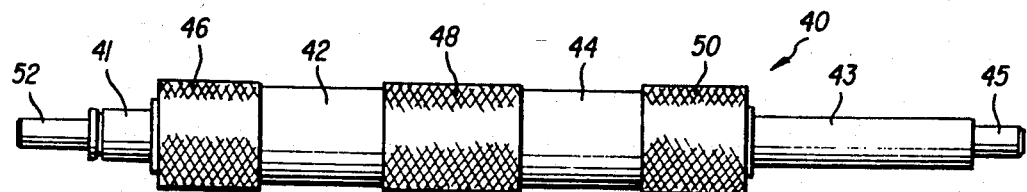
FIG. 6 shows a view from the same direction as the view of FIG. 2 of the guide roller of the present invention.

With particular reference to FIGS. 2 and 6, the guide roller 40 is seen to include three regions 46, 48 and 50 of a first diameter each having a knurled outer surface. The regions 46, 48 are separated by a smooth surfaced region 42 of slightly lesser diameter, while the regions 48 and 50 are separated by a smooth surfaced region 44 of lesser diameter than the diameter of the regions 48, 50. The diameter of the region 42 is the same as the diameter of the region 44. As seen in FIG. 6, the axle 41 includes a reduced diameter outer portion 52 which is designed to couple with the gear 55 hub 56.

With reference back to FIG. 1, it is seen that the platform has raised regions 3, 5, 7 aligned with the regions 46, 48 and 50 of the roller 40, as well as lower regions 4, 6 aligned with the lesser diameter regions 42, 44 of the roller 40. This configuration is for a purpose to be described in greater detail hereinafter.

Figure 11:
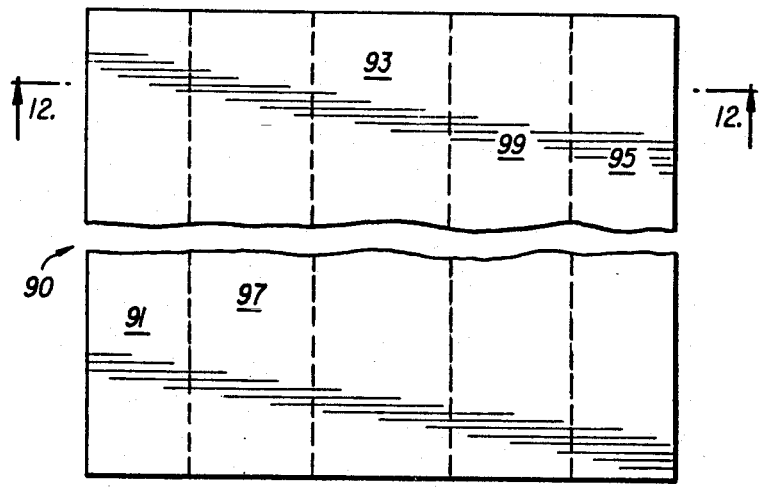
FIG. 11 shows a top view of a carrier device forming a part of the present invention.
Figure 12:
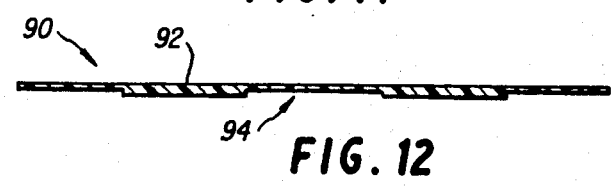
FIG. 12 shows a cross-sectional view along the line 12—12 of FIG. 11.

With reference to FIGS. 11 and 12, carrier means consisting of a carrier device 90 is seen to be of generally rectangular shape and includes three regions 91, 93 and 95 of one thickness and regions 97, 99 which are of a second thickness. The regions 91, 93 are separated by the region 97, while the regions 93 and 95 are separated by the region 99.

As best seen in FIG. 12, the region 97 is of the same thickness as the region 99, whereas the regions 91, 93 and 95 are of equal thickness. Furthermore, FIG. 12 shows that the regions 97 and 99 are thicker than the regions 91, 93 and 95.

In the preferred embodiment of the carrier device 90, it is made of polypropylene or vinyl in an extrusion process.

Comparison of FIGS. 12 and 6 reveals that the relationship between the regions 91, 97, 93, 99 and 95 of the carrier device 90 corresponds with the relationship between the surfaces 46, 42, 48, 44 and 50, respectively, of the guide roller 40. Thus, it is easy to envision that the carrier device 90 with its flat top surface 92 and bottom surface 94 of varied thickness due to the regions 91, 97, 93, 99 and 95 may easily be inserted between the guide roller 40 and the cutter roller 60 as seen in the view of FIG. 2, with the guide roller 40 guiding the bottom surface 94 of the carrier device 90 and with the top surface 92 of the carrier device 90 facing the cutter roller 60. I such position, a piece of skin which is to be cut by the cutter roller 60 may be placed on the flat top surface 92 of the carrier device 90 and may be indexed through the device 10 by rotation of the handle 47 to cause corresponding rotations of the guide roller 40, thus pulling the carrier device 90 therethrough with the skin placed on the top surface 92 of the carrier device 90 being engaged by the cutter roller 60 to cut a predetermined pattern on the surface thereof.

Alternatively, the manual actuation described above may be replaced with motorized activation. In this regard, for example, a motorized actuator may be coupled to the coupling portion 45 and may be selectively operated to move the carrier device 90 between the rollers 40 and 60. Of course, manual and motorized actuation may be alternately employed where desired.

Figure 13:
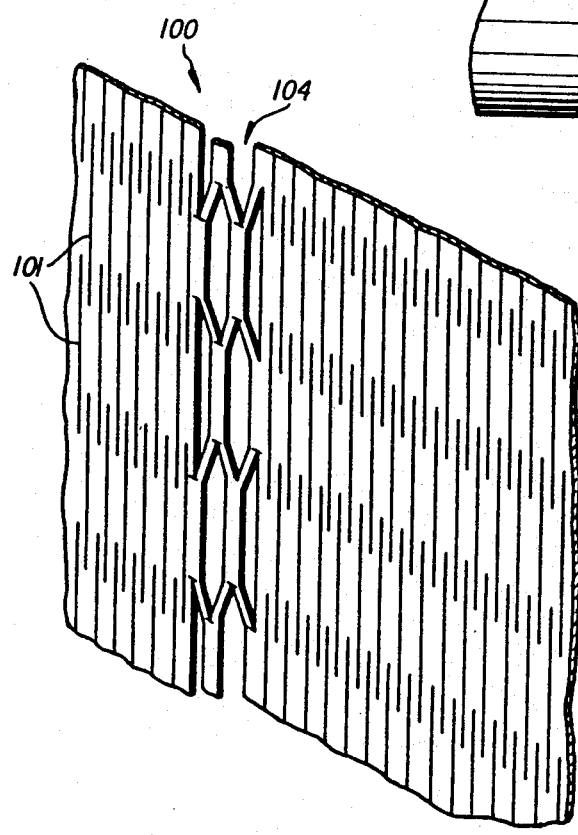
FIG. 13 shows a top view of a piece of skin which has been carried through the cutter roller of the present invention by the carrier device thereof.

With reference to FIG. 13, a piece of skin 100 which has been indexed through the device 10 is seen to include a plurality of parallel rows 101 of cuts. Each such row is discontinuous from one end to another, including portions which are cut alternating with uncut portions. Of further note is the fact that to each side of a cut portion of a row, an uncut portion of an adjacent row is provided and, conversely, to each side of an uncut portion of a row, a cut portion of an adjacent row is provided.

With such a cut pattern being provided on a piece of skin having been treated by indexing through the inventive device 10, the skin may be stretched to a desired ratio of expansion, as shown at 104.

As seen in FIG. 2, the pattern of grooves on the surface of the cutter roller 60 is generally designated by the reference numeral 64. The cutting ratio provided by the surface 64 is determined through the machining of the cutter roller. In machining a particular cutter roller, a cylindrical roller is placed in a turning mechanism and is rotated while a machining tool is indexed across the face thereof to provide a series of cutting edges 62 which are parallel to each other at a specific interval between one another. These cutting edges consist of a plurality of rings which are parallel to one another across the face of the cutter 60.

In order to produce intermittent cutting action on specific regions of the skin, a second operation is required in making the cutter roller. In this regard, thread-like slots 64 are machined into the surface of the cutter roller which traverse the face of the cutter in a predetermined special fashion. The particular pitch of these slots determines the ratio of expansion of skin which is cut through the use of the inventive cutter roller. For example, a nine lead design results in a 1.5:1 ratio, whereas a two lead design results in a 9:1 ratio.

This second operation is carried out using one or more machining tools simultaneously moved across the face of the cutter roller as it is rotating in the turning device. The number of machining tools which are employed, whether simultaneously or sequentially, helps to determine the ratio.

With reference to FIGS. 7, 8, 9 and 10, the parallel cutting edges 62 are shown, as are shown the spiral-shaped slots 64 which cause the cutter edges to become discontinuous in a manner determining the ratio of expansion of skin which is cut through use of the inventive device.

Figure 7:
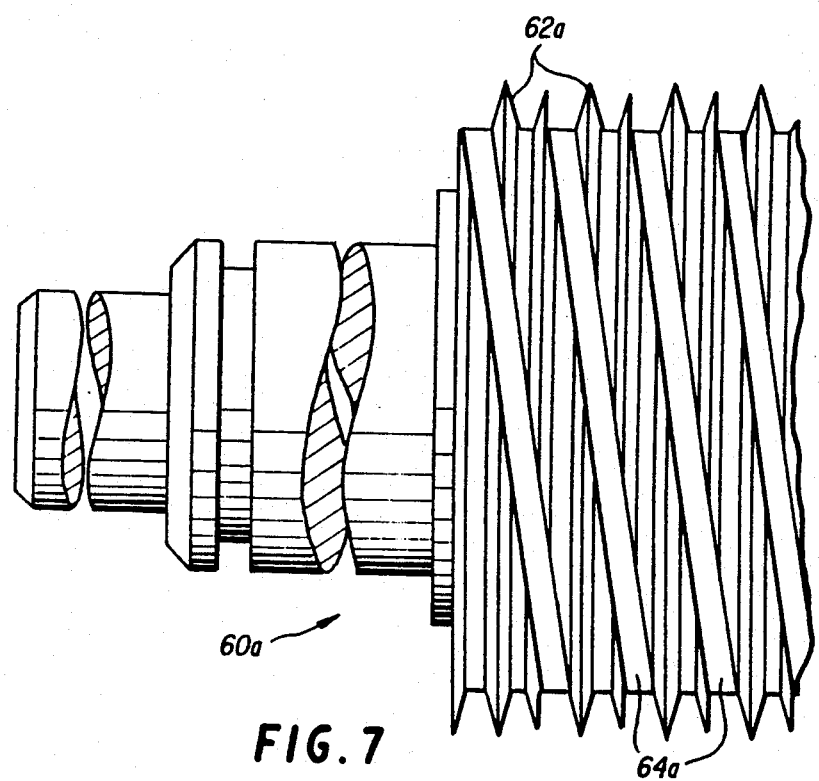
FIGS. 7, 8, 9 and 10, respectively show views of different embodiments of the cutter roller with each said figure showing a cutter roller with a unique number of grooves cut therein.
Figure 8:
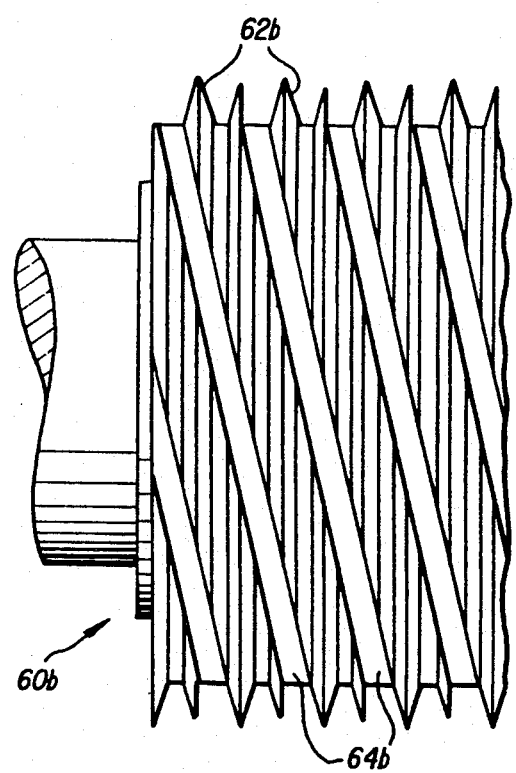

FIG. 7 shows spiral grooves 64a formed through operation of two machining tools simultaneously. FIG. 8 shows a cutter roller 60b having spiral grooves 64b formed by the operation of three machining tools simultaneously.

Figure 9:
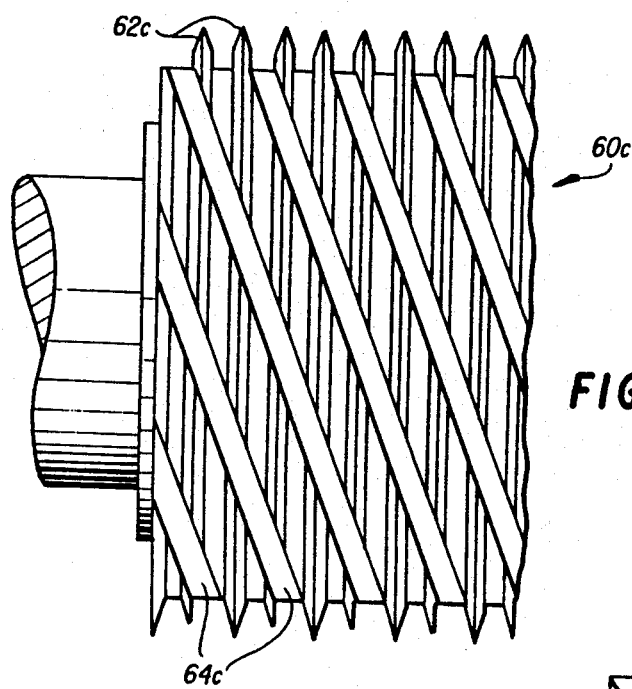

FIG. 9 shows a cutter roller 60c having spiral grooves 64c formed through the operation of five machining tools simultaneously.

Figure 10:
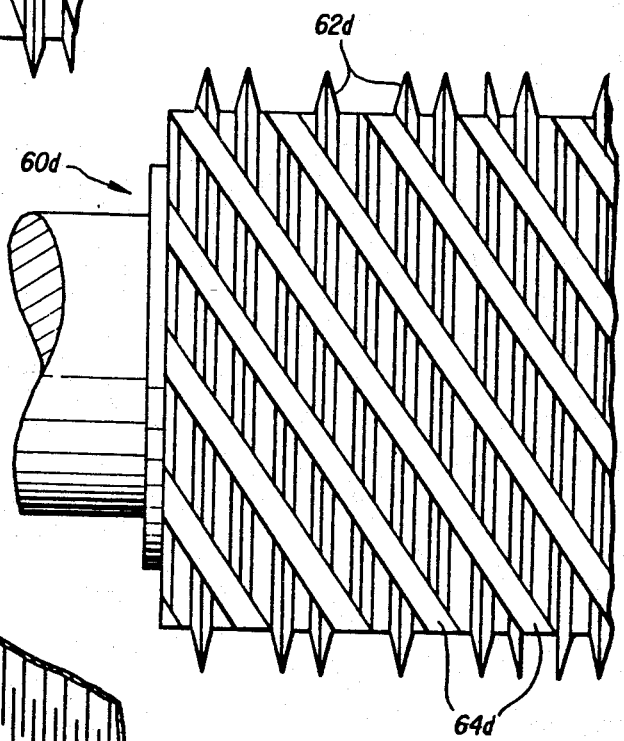

Finally, FIG. 10 shows a cutter roller 60d having spiral grooves 64d formed by the operation of nine machining tools simultaneously.

As explained above, the discontinuous nature of the cutting edges as formed by the spiral-shaped grooves causes the discontinuous cuts shown particularly in FIG. 13.

Figure 3:
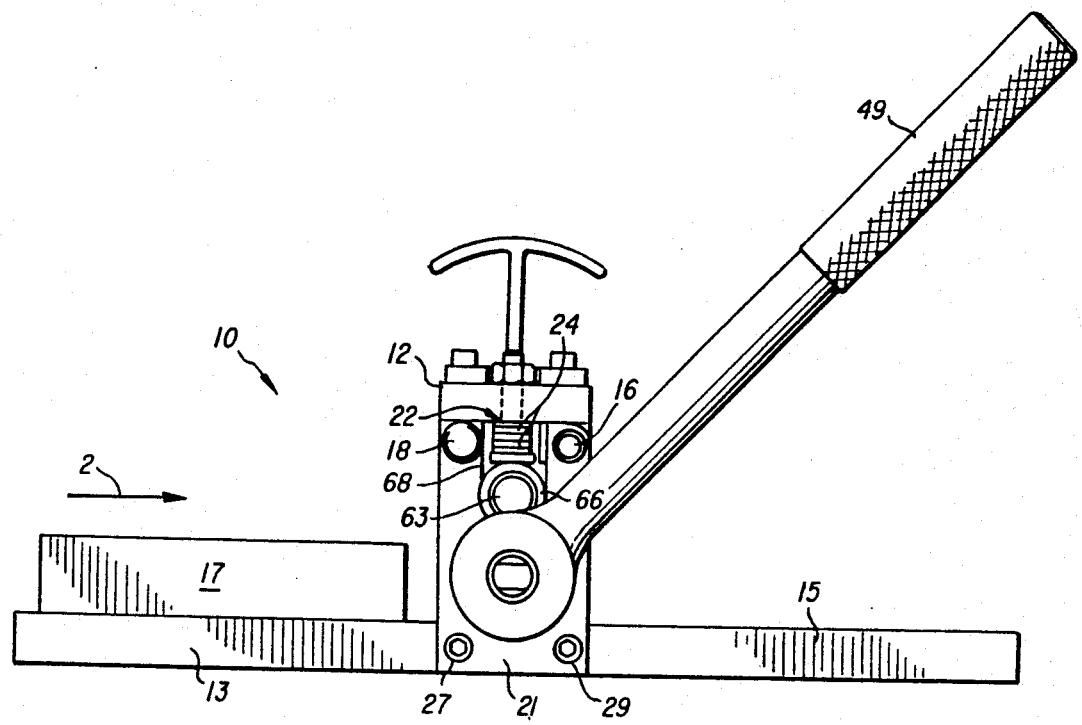
FIG. 3 shows a right side view of the present invention.

As best seen in FIG. 3, the cutter roller 60 is supported for rotation about a pair of bearings 66, of which one is shown in FIG. 3. A U-shaped recess 68 in the support 21 removably receives the bearing 66 and supports the bearing 66 to allow rotation of the axle 63 and thus the roller 60 with respect thereto.

As best seen from comparison of FIGS. 3 and 5, resilient biasing means 22 in the form of a plurality of stacked Bellville washers 24 is mounted on the cover 12 of the housing 11. As best seen in FIGS. 3-5, the cover 12 is pivotally mounted on the supports 19, 21 by virtue of pivots 14, 16 of which the pivot 14 is shown in FIG. 4 and FIG. 5, and of which the pivot 16 is seen in FIG. 3. FIG. 5 shows the cover 12 pivoted to a position allowing removal of the cutter roller 60 from between the supports 19, 21.

As best seen in FIG. 3, when the cover 12 is pivoted to the closed position, movements of the roller 60 are resisted by the resilient biasing force of the Bellville washers 24. However, slight movements of the bearing 66 and, thus, the roller 60 in the upward direction in the view of FIGS. 2-5 are possible. The biasing means 22 are provided to allow such slight upward movements of the cutter roller 60 to allow accommodation for skin of varying thickness which may be indexing between the cutter roller 60 and the guide roller 40, as carried by the carrier device 90. Of course, the biasing means 22 also allows accommodation for variances in the thickness of the carrier device 90. As should be understood, with particular comparison of FIGS. 3 and 4, a resilient biasing means 22 is provided on each support 19, 21 to support each bearing 66 of the cutter roller 60.

With the inventive apparatus 10 having been described in detail hereinabove, the preferred mode of operation thereof will now be described. When it is desired to utilize the inventive apparatus 10 to cut and thereafter expand skin for use in a grafting procedure, firstly, the desired cutting roller 60 is installed in the device 10 by first pivoting the cover 12 to the position shown in FIG. 5 and inserting the desired cutter roller 60 into the recesses provided therefor. Each cutter roller 60 includes a pair of bearings 66, as well as a gear 65 designed to enmesh with the gear 55 of the guide roller 40.

With the desired cutter roller 60 having the desired ratio so inserted, the cover 12 may be pivoted to the position shown in FIGS. 2, 3 and 4 and may be tightened in that position by provision of the locking pins 18. If desired, the locking pins 18 may be threadably tightened to the position shown particularly in FIG. 2.

With the desired cutter roller 60 having been so installed, a carrier device 90 is placed on the pedestal 17 with the surface 94 thereof facing downwardly. The regions 91, 93 and 95 of the carrier device 90 are guided on the regions 3, 5, and 7 of the platform while the regions 97 and 99 of the carrier device 90 are guided on the regions 4 and 6 of the platform 17. In this way, the carrier device 90 is guided into the space between rollers 40 and 60. The carrier device 90 is then moved in the direction of the arrow 2 (FIG. 3) with the portions 97, 99 thereof enmeshing with the surfaces 42, 44 respectively of the guide mechanism 40, and with the surfaces 91, 93, 95 of the carrier device 90 enmeshing with the respective surfaces 46, 48 and 50 of the guide roller 40. In such configuration, a piece of skin (not shown) is placed on the surface 92 of the carrier device 90 and through rotations of the handle 47, is conveyed in the direction of the arrow 2 shown in FIG. 3 to thereby move under the cutting surface 64 of the roller 60. Continued rotation of the handle 47 causes the carrier device 90 and the skin placed thereon to be indexed completely through the device 10 with the pattern of cuts formed thereon corresponding to that which is best illustrated in FIG. 13.

Thereafter, the skin 100 may be expanded by stretching it as allowed by the cuts 101 and may thereafter be placed on an area where a graft is being performed.

In this way, expansion ratios which have not been possible to accomplish using prior art devices may be carried out in an easy and effective manner.

As such, an invention has been described in terms of a preferred embodiment thereof, which fulfills each and every one of the objects of the invention as set forth hereinabove and provides a new and improved mechanism which may be effectively employed to perform cuts on a piece of skin to best facilitate the use of the said piece of skin in a grafting operation.

Of course, various changes, modifications and alterations in the teachings of the present invention may be contemplated by those skilled in the art without departing from the intended spirit and scope of the present invention. As such, it is intended that the present invention only be limited by the terms of the appended claims.

I claim:

1. A skin graft preparation system allowing varying of a pattern of cuts in skin which is treated thereby, comprising:
   a) a skin graft preparation apparatus having a housing;
   b) support means on said housing for supporting roller means;
   c) said roller means comprising a guide roller and one of a plurality of cutting rollers, each of said cutting roller comprising an elongated cylindrical body, a multiplicity of spaced annular lands having sharp peripheries and lying in parallel planes, and at least one thread-like continuous groove formed in said body and causing discontinuities in said lands;
   d) said plurality of cutting rollers including at least a first cutting roller providing a first pattern of cuts and a second cutting roller providing a second pattern of cuts;
   e) said support means supporting said guide roller and one of said cutting rollers;
   f) openable cover means on said support means for allowing, in an open position thereof, removal of a said cutting roller and replacement with another of said cutting rollers;
   g) carrier means having a continuously flat skin supporting surface for carrying a piece of skin through a gap between said guide roller and said one of a plurality of cutting rollers with said piece of skin facing said one of said plurality of cutting rollers;
   h) said piece of skin being advanced through said roller means on said carrier means whereby said one of a plurality of cutting rollers engages said piece of skin to cut a desired pattern of cuts thereon.

2. The invention of claim 1, wherein said plurality of cutting rollers further comprises a third cutting roller providing a third pattern of cuts and a fourth cutting roller providing a fourth pattern of cuts.

3. The invention of claim 2, wherein cutting ratios of said cutting rollers range from a cutting ratio permitting expansion of a piece of skin to cover about one and one-half times the area covered prior to being cut, to a cutting ratio permitting expansion of a piece of skin to cover about nine times the area covered prior to being cut.

4. The invention of claim 3, wherein each cutting ratio is determined by a particular pitch of one or more thread-like grooves formed on a particular cutting roller.

5. The invention of claim 1, wherein said at least one groove comprises two parallel grooves.

6. The invention of claim 1, wherein said at least one groove comprises three parallel grooves.

7. The invention of claim 1, wherein said at least one groove comprises five parallel grooves.

8. The invention of claim 1, wherein said at least one groove comprises nine parallel grooves.

9. The invention of claim 1, wherein each of said cutting rollers includes a like portion of drive means for driving said roller means whereby said plurality of cutting rollers are interchangeable.

10. A skin graft preparation apparatus, comprising:
    a) a housing;
    b) support means on said housing for supporting roller means;
    c) roller means supported on said support means and comprising a guide roller and a cutting roller;
    d) openable cover means on said support means for allowing, in an open position thereof, removal and replacement of said cutting roller;
    e) actuator means for said roller means including an actuator coupled to one of said rollers and drive means drivingly coupling said rollers together whereby rotations of one of said rollers result in rotations of another of said rollers;
    f) further, wherein said cutting roller comprises one of a plurality of cutting rollers, each of which has a unique cutting pattern thereon and each of said cutting rollers comprising an elongated cylindrical body, a multiplicity of spaced annular lands having sharp peripheries and lying in parallel planes, and at least one thread-like continuous groove formed in said body and causing discontinuities in said lands.

11. The invention of claim 10, wherein a particular said unique cutting pattern is determined by the particular pitch of thread-like grooves formed on said cutting roller.

12. The invention of claim 11, wherein the thread-like grooves are spiral and wherein the plurality of cutters include at least two of the following cutters: a cutter having spiral grooves formed through operation of two machining tools simultaneously; a cutter having spiral grooves formed by operation of three machining tools simultaneously; a cutter having spiral grooves formed through the operation of five machining tools simultaneously; and a cutter having spiral grooves formed by the operation of nine machining tools simultaneously.

13. The invention of claim 10, wherein said unique cutting pattern is within the range permitting expansion of a piece of cut skin to cover an area from one and one-half to nine times the area covered by said piece of cut skin prior to expansion.

14. The invention of claim 10, wherein each said cutting roller incorporates a like-portion of said drive means therewith whereby cutting rollers of differing cutting patterns are interchangeable.

15. The invention of claim 10, wherein said cover means is pivotably mounted on said support means.

* * * * *